United States Patent
Nishimura et al.

(10) Patent No.: US 8,295,566 B2
(45) Date of Patent: Oct. 23, 2012

(54) MEDICAL IMAGE PROCESSING DEVICE AND MEDICAL IMAGE PROCESSING METHOD

(75) Inventors: Hirokazu Nishimura, Hachioji (JP); Hideki Tanaka, Tama (JP); Kenji Nakamura, Chiba (JP); Ryoko Inoue, Hachioji (JP); Miho Sawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1077 days.

(21) Appl. No.: 12/208,821

(22) Filed: Sep. 11, 2008

(65) Prior Publication Data

US 2009/0074269 A1 Mar. 19, 2009

Related U.S. Application Data

(63) Continuation of application No. PCT/JP2007/053588, filed on Feb. 27, 2007.

(30) Foreign Application Priority Data

Mar. 16, 2006 (JP) .................................. 2006-073184

(51) Int. Cl.
*G06K 9/00* (2006.01)

(52) U.S. Cl. ........................................ 382/128; 382/190
(58) Field of Classification Search .................. 382/128, 382/190

See application file for complete search history.

(56) References Cited

U.S. PATENT DOCUMENTS

| 2003/0048931 A1 | 3/2003 | Johnson et al. |
| 2005/0069184 A1 | 3/2005 | Kasai |
| 2005/0201599 A1 | 9/2005 | Matsui |

FOREIGN PATENT DOCUMENTS

| JP | 2004-180932 | 7/2004 |
| JP | 2005-095501 | 4/2005 |
| JP | 2005-192880 | 7/2005 |
| JP | 2005-253685 | 9/2005 |
| WO | WO 2005/084520 A1 | 9/2005 |
| WO | WO 2006/000738 A1 | 1/2006 |

OTHER PUBLICATIONS

Okatani, T. et al., "Reconstructing Shape from Shading with a Point Light Source at the Projection Center-Shape Reconstruction from an Endoscopic Image", Computer vision 98-4, (Jan. 18, 1996), pp. 19-26.

Kimura, T. et al., "A study on automated detection of colonic polyps from 3D abdominal CT images based on shape", Technical Report of IEICE MI2003-102 (Jan. 2004), pp. 29-34.

Extended Supplementary European Search Report dated Jul. 21, 2010.

*Primary Examiner* — Phat X Cao

(74) *Attorney, Agent, or Firm* — Scully, Scott, Murphy & Presser, P.C.

(57) ABSTRACT

An image processing device includes; a lesion candidate region detecting section that detects a lesion candidate region based on at least one color signal in a medical image including a plurality of color signals; an incidental region detecting section that detects an incidental region that arises because of incidental attributes accompanying a lesion from the medical image; and a detection standard changing section that changes a detection standard when detecting a lesion from the lesion candidate region in accordance with a detection result of the incidental region.

12 Claims, 10 Drawing Sheets

MEDICAL IMAGE PROCESSING DEVICE AND MEDICAL IMAGE PROCESSING METHOD

CROSS REFERENCE TO RELATED APPLICATION

This application is a continuation application of PCT/JP2007/053588 filed on Feb. 27, 2007 and claims benefit of Japanese Application No. 2006-073184 filed in Japan on Mar. 16, 2006, the entire contents of which are incorporated herein by this reference.

BACKGROUND OF THE INVENTION

1. Field of the Invention

The present invention relates to a medical image processing device and a medical image processing method that are suitable for detecting a lesion candidate region from a medical image to detect a lesion such as a polyp.

2. Description of the Related Art

In recent years, endoscopes have been widely used, for example, for medical examination and diagnosis in the field of medical treatment.

In such cases, the physician inserts the insertion portion of the endoscope inside a body cavity such as the colon of the patient to pick up images inside the body cavity using image pickup means provided at the distal end portion of the insertion portion. The physician performs endoscopy such as an examination or diagnosis of a lesion such as a polyp by observing the endoscopic images that are displayed on a monitor. In this case, since it is desirable that the physician causes little pain or distress to the patient and also performs endoscopy smoothly, the burden on the physician increases.

Therefore, for example, Japanese Patent Application Laid-Open Publication No. 2004-180932 as a first example of the prior art discloses an arrangement in which lesion candidates for the same region of interest are detected by a first image diagnosis apparatus comprising an X-ray CT apparatus or the like and a second image diagnosis apparatus such as an X-ray TV apparatus, respectively. A detection result in which these two detection results are compared and combined is then shown to the physician. It is thereby possible to prevent an oversight by the physician.

Further, as a second example of the prior art, Japanese Patent Application Laid-Open Publication No. 2005-192880 discloses an image processing method that detects a lesion candidate region from an endoscopic image based on color tone information.

In images in which the inside of a body cavity is optically observed, such as in endoscopic images, since color information can also be obtained, it is desirable to also utilize the color information for lesion detection and the like.

The second example of the prior art is arranged to utilize color information and contour information to detect hemorrhaging and reddening as well as elevations and concavities and the like.

SUMMARY OF THE INVENTION

A first medical image processing device according to the present invention comprises a lesion candidate region detecting section that detects a lesion candidate region based on at least one color signal in a medical image including a plurality of color signals, an incidental region detecting section that detects an incidental region that arises because of incidental attributes that accompany a lesion from the medical image, and a detection standard changing section that changes a detection standard when detecting a lesion from the lesion candidate region according to a detection result of the incidental region.

A second medical image processing device according to the present invention comprises a lesion candidate region detecting section that detects a lesion candidate region based on at least one color signal in a medical image including a plurality of color signals and an incidental region detecting section that detects an incidental region that arises because of incidental attributes that accompany a lesion from the medical image, wherein lesion detection is performed based on existence or non-existence of a region in which a lesion candidate region that is detected by the lesion candidate region detecting section and an incidental region that is detected by the incidental region detecting section correlate.

Further, a medical image processing method according to the present invention includes a lesion candidate region detection step that detects a lesion candidate region based on at least one color signal in a medical image comprising a plurality of color signals, an incidental region detection step that detects existence or non-existence of an incidental region that arises because of incidental attributes that accompany a lesion from the medical image, and a detection standard changing step that changes a detection standard when detecting a lesion from the lesion candidate region according to a detection result regarding existence or non-existence of the incidental region.

DESCRIPTION OF THE PREFERRED EMBODIMENT(S)

Figure 1:
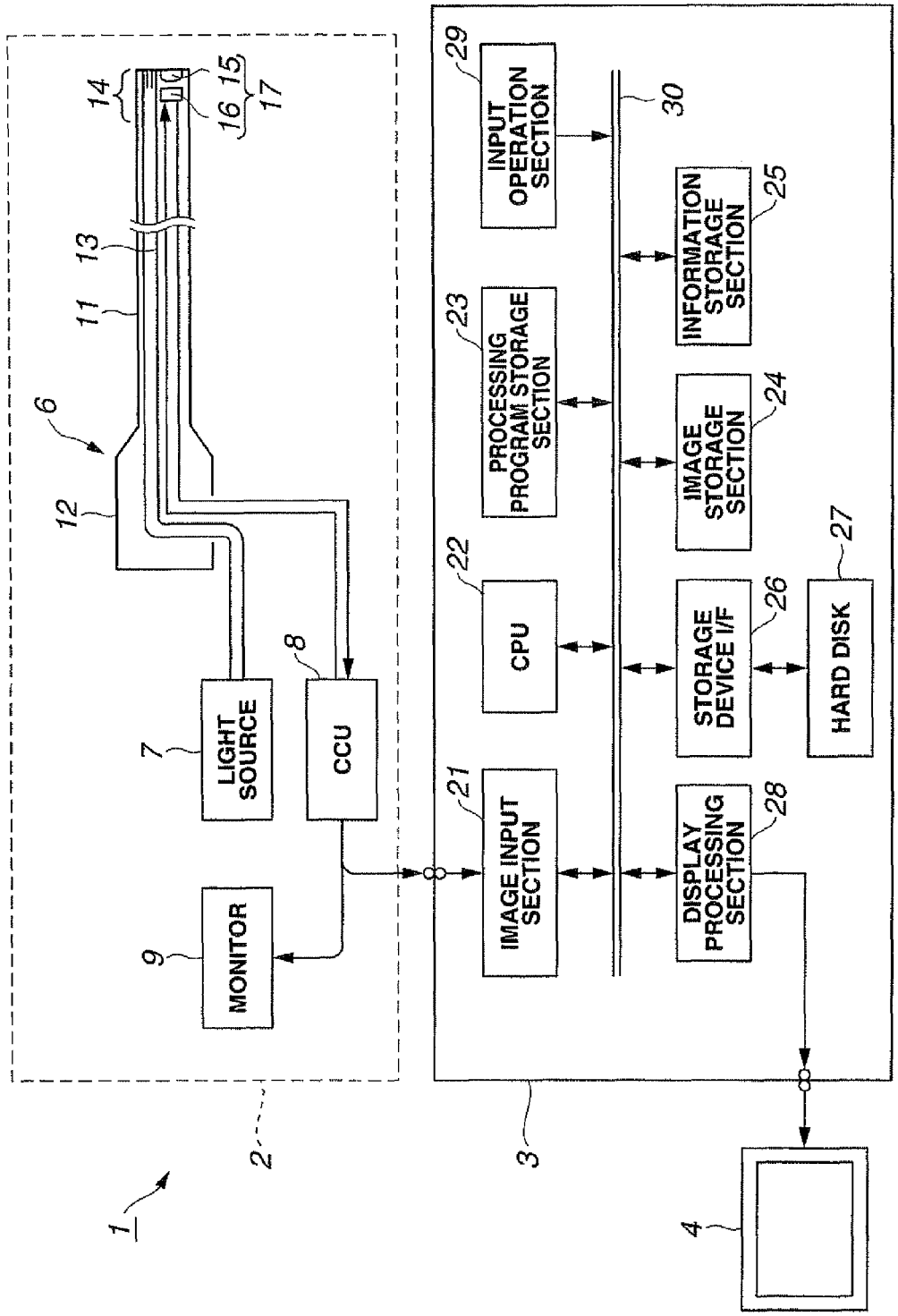
FIG. 1 is a block diagram that illustrates the configuration of an endoscope system according to Embodiment 1 of the present invention.

Hereunder, embodiments of the present invention are described referring to the drawings.

Embodiment 1

Figure 2:
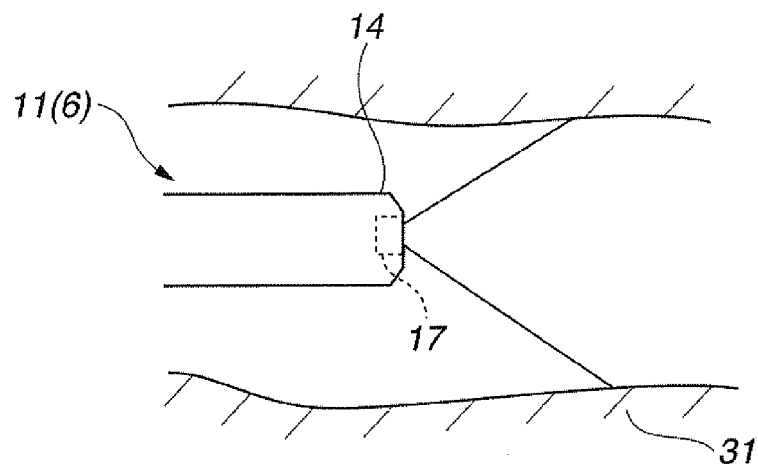
FIG. 2 is a view that illustrates a state in which an endoscope is inserted into a tubular region such as a colon to pick up images according to Embodiment 1 of the present invention.
Figure 3A:
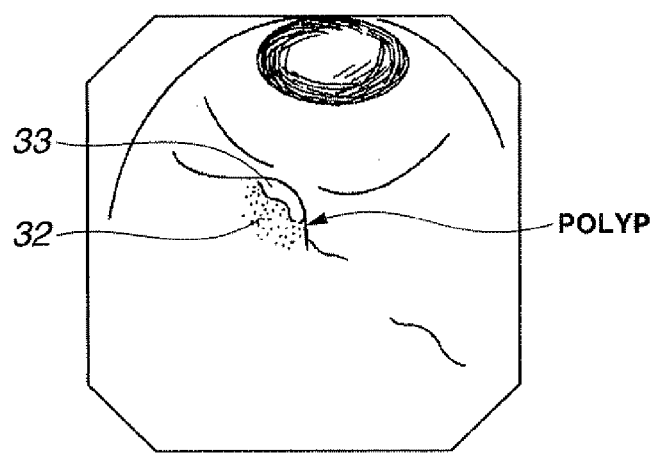
FIG. 3A is a view that illustrates an example of an endoscopic image that is picked up by the image pickup apparatus provided in the endoscope shown in FIG. 2.
Figure 3B:
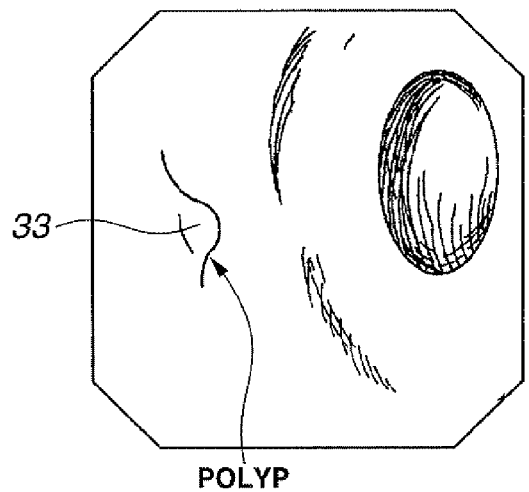
FIG. 3B is a view that illustrates an example of an endoscopic image that is picked up by the image pickup apparatus provided in the endoscope shown in FIG. 2.
Figure 4:
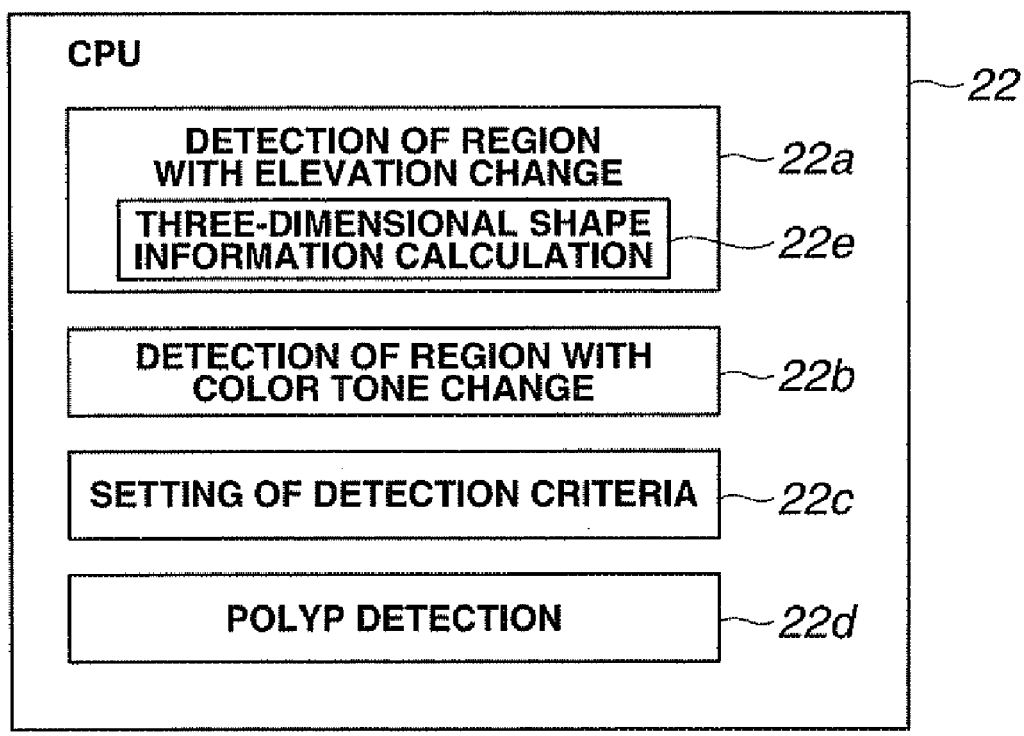
FIG. 4 is a block diagram that illustrates image processing functions performed by a CPU according to Embodiment 1 of the present invention.
Figure 5:
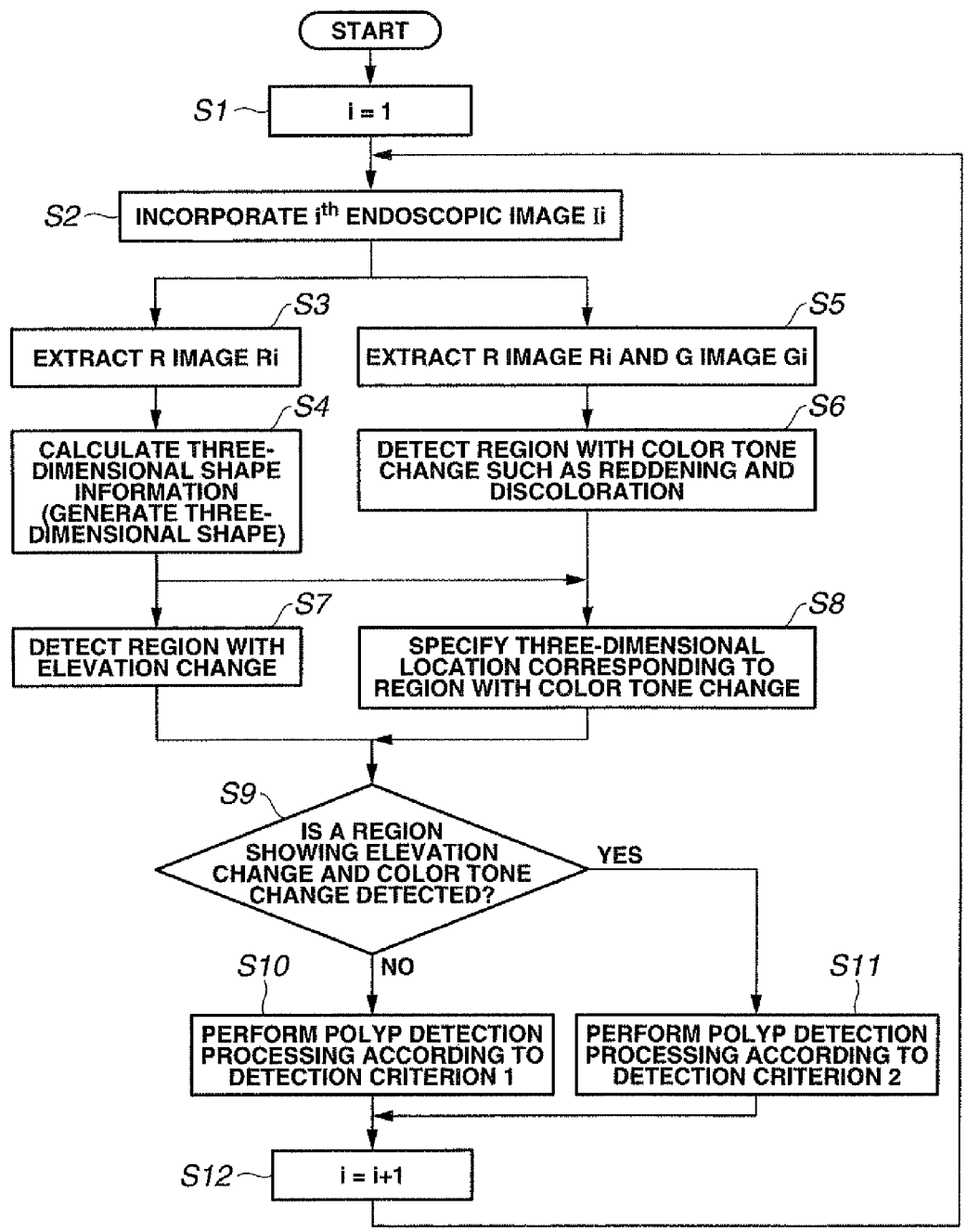
FIG. 5 is a flowchart that illustrates a process to detect a polyp as an elevated lesion by image processing according to Embodiment 1 of the present invention.
Figure 6:
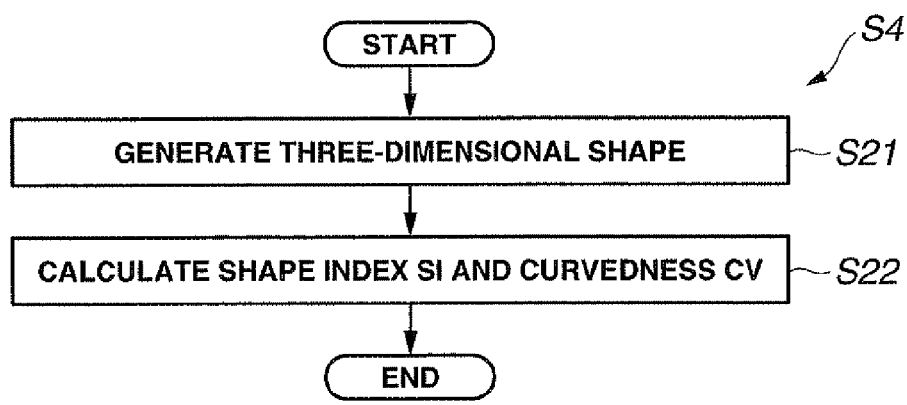
FIG. 6 is a flowchart that illustrates a process to calculate three-dimensional shape information at step S4 in FIG. 5.
Figure 7:
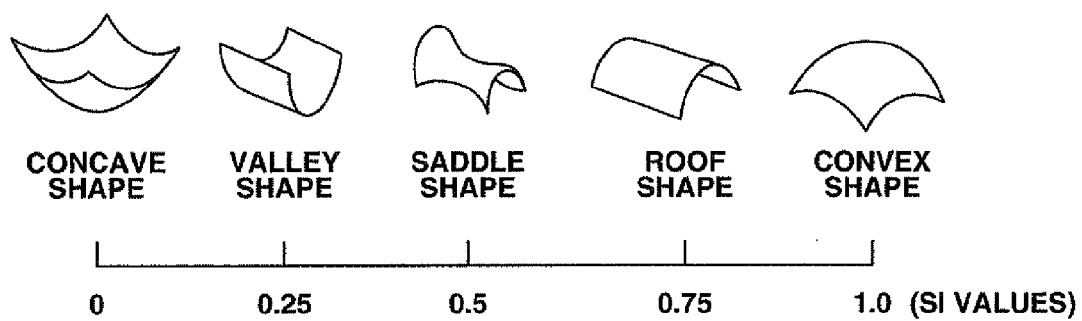
FIG. 7 is a view that illustrates curved shapes according to values of a shape index SI that are calculated according to step S12 in FIG. 6.
Figure 8:
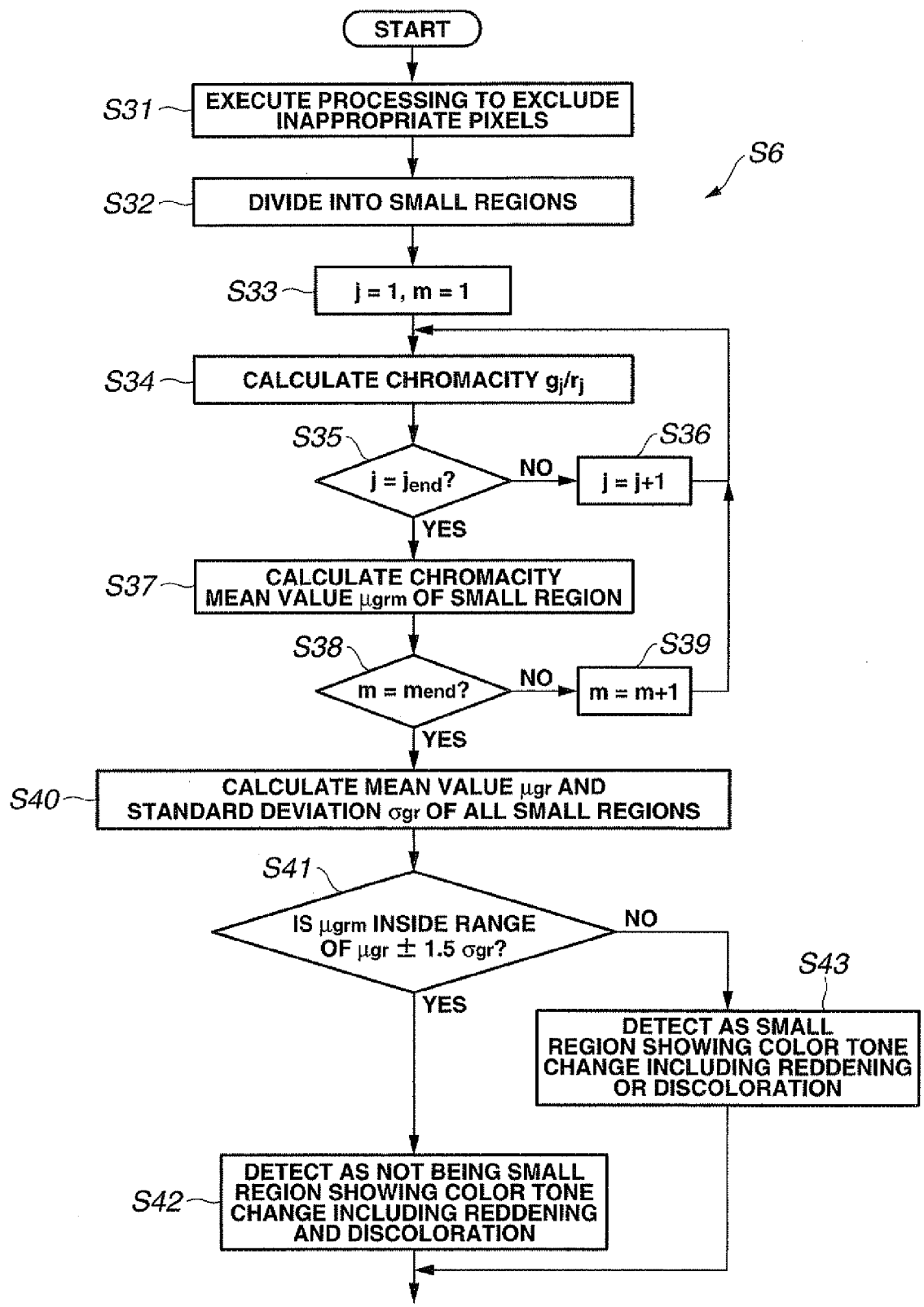
FIG. 8 is a flowchart that illustrates the processing contents at step S6 in FIG. 5.

FIG. 1 to FIG. 8 relate to Embodiment 1 of the present invention. FIG. 1 is a block diagram that illustrates the configuration of an endoscope system. FIG. 2 is a view that illustrates a state in which an endoscope is inserted into a tubular region such as a colon to pick up images. FIG. 3A is a view that illustrates an example of an endoscopic image that is picked up by the image pickup apparatus provided in the endoscope shown in FIG. 2. FIG. 3B is a view that illustrates an example of an endoscopic image that is picked up by the image pickup apparatus provided in the endoscope shown in FIG. 2. FIG. 4 is a block diagram that illustrates image processing functions performed by a CPU. FIG. 5 is a flowchart that illustrates a process to detect a polyp as an elevated lesion by image processing. FIG. 6 is a flowchart that illustrates a process to calculate three-dimensional shape information at step S4 in FIG. 5. FIG. 7 is a view that illustrates curved shapes according to values of a shape index SI that are calculated according to step S12 in FIG. 6. FIG. 8 is a flowchart that illustrates the processing contents at step S6 in FIG. 5.

An endoscope system 1 shown in FIG. 1 includes an endoscopic observation apparatus 2, an endoscopic image processing device (hereunder, referred to simply as "image processing device") 3 such as a personal computer that performs image processing with respect to an endoscopic image obtained by the endoscopic observation apparatus 2, and a display monitor 4 that displays an image that is subjected to image processing by the image processing device 3.

The endoscopic observation apparatus 2 includes an endoscope 6 that is inserted inside a body cavity, a light source 7 that supplies an illumination light to the endoscope 6, a camera control unit (abbreviated as "CCU") 8 that performs signal processing with respect to image pickup means of the endoscope 6, and a monitor 9 that displays an endoscopic image that is picked up with the image pickup device by input of a video signal that is outputted from the CCU 8.

The endoscope 6 includes an insertion portion 11 that is inserted into a body cavity, and an operation portion 12 that is provided at the rear end of the insertion portion 11. A light guide 13 that transmits an illumination light is passed through the inside of the insertion portion 11.

A light source 7 is connected to the rear end of the light guide 13. An illumination light that is supplied from the light source 7 is transmitted by the light guide 13. The transmitted illumination light is emitted from a distal end face of an illumination window provided in a distal end portion 14 of the insertion portion 11 and illuminated onto an object such as a diseased part.

An image pickup apparatus 17 comprises an observation lens 15 that is mounted in an observation window adjoining the illumination window and, for example, a charge coupled device (abbreviated as "CCD") 16 as a solid state image pickup device that is disposed at an image formation position of the observation lens 15. An optical image that is formed on the image pickup surface of the CCD 16 is subjected to photoelectric conversion by the CCD 16.

The CCD 16 is connected to the CCU 8 via a signal wire. When a CCD driving signal is applied from the CCU 8, the CCD 16 outputs an image signal that has undergone photoelectric conversion. The image signal is subjected to signal processing by a video processing circuit inside the CCU 8 and convened into a video signal. The video signal is outputted to the monitor 9 to display an endoscopic image on the screen of the monitor 9. The video signal is also inputted to the image processing device 3.

The image processing device 3 includes an image inputted section 21 into which is input a video signal corresponding to an endoscopic image that is inputted from the endoscopic observation apparatus 2, a CPU 22 as a central processing unit that performs image processing corresponding to image data that is input from the image input section 21, and a processing program storage section 23 that stores a processing program (control program) that causes the CPU 22 to execute image processing.

The image processing device 3 also includes an image storage section 24 that stores image data and the like that is inputted from the image inputted section 21, an information storage section 25 that stores information and the like that is processed by the CPU 22, a hard disk 27 as a storage device that stores image data and information and the like that is processed by the CPU 22 via a storage device interface 26, a display processing section 28 that performs display processing for displaying image data and the like that is processed by the CPU 22, and an input operation section 29 comprising a keyboard or the like through which a user inputs data such as image processing parameters or an instruction operation.

A video signal that is generated by the display processing section 28 is displayed on the display monitor 4 to thereby display a processed image that has undergone image processing on the screen of the display monitor 4. In this connection, the image input section 21, the CPU 22, the processing program storage section 23, the image storage section 24, the information storage section 25, the storage device interface 26, the display processing section 28, and the input operation section 29 are mutually connected via a data bus 30.

According to the present embodiment, as shown in FIG. 2, an insertion portion 11 of a forward-viewing endoscope 6 is inserted into, for example, a tubular region (tubular organ) such as a colon 31 and images are picked up by the image pickup apparatus 17.

FIG. 3A and FIG. 3B illustrate examples of a two-dimensional endoscopic image having a polyp as an elevated lesion that is picked up by the endoscope 6.

FIG. 3A is a view that shows an endoscopic image having a polyp accompanied by a reddened color tone portion 32. The top part of the polyp is a discolored portion 33 that is a white color.

FIG. 3B is a view showing an endoscopic image having a polyp accompanied by a discolored portion 33 that is a white color in a wider area than in the example shown in FIG. 3A.

With respect to a polyp as an elevated lesion of this kind, cases often occur in which a color tone change such as a reddening tone or a white tone (discoloration) occurs as an incidental attribute. According to the present embodiment, the existence or non-existence of a color tone change region that presents this kind of color tone change as an incidental region is detected or judged. Further, a detection standard to be utilized when performing polyp detection or judgment thereafter is changed (or controlled) in accordance with the detection result for the color tone change region. More specifically, the threshold value of the detection standard is changed.

Further, according to the present embodiment, to improve the accuracy of the above described polyp detection, a three-dimensional shape of an examination target region (for example, an inner surface having a luminal shape) is estimated based on the two-dimensional endoscopic image that is picked up. Using the information for the estimated three-dimensional shape, a region with an elevation change is detected as a polyp candidate.

With respect to a portion corresponding to a detected region with an elevation change (including the periphery thereof), the threshold value of the detection standard for performing polyp detection is changed in accordance with the result of detection of an incidental region that is accompanied by the above described color tone change.

More specifically, when accompanied by a color tone change, as the detection standard to be applied when performing the polyp detection according to an elevation change, a detection standard is applied for which the detection conditions are more relaxed than in a case that is not accompanied by a color tone change.

As described later, in a case in which polyp detection is performed using the method illustrated in FIG. 5, polyp detection (judgment) is performed according to an elevation change by employing a detection standard 1 as a threshold value in a case that is not accompanied by a color tone change, and employing a detection standard 2, for which the detection conditions are more relaxed compared to the detection standard 1, as a threshold value in a case that is accompanied by a color tone change.

By performing polyp detection with image processing in this manner, a polyp detection result can be obtained accurately (or with high reliability).

FIG. 4 is a view that illustrates image processing functions that are performed by the CPU 22 inside the image processing device 3 of the present embodiment. The CPU 22 has a region with elevation change detection function 22a as lesion candidate region detecting means that detects a region with an elevation change as an elevated lesion candidate region based on contrast information (or luminance information) from endoscopic image data that is picked up, a region with color tone change detection function 22b as incidental region detecting means that detects a color tone change region from a plurality of color signals of an endoscopic image, a polyp detection function 22d that detects a polyp as an elevated lesion with respect to a region with an elevation change that is detected, and a detection standard setting function 22c as detection standard changing means that changes a polyp detection standard depending on whether or not there is an accompanying color tone change region when performing the polyp detection.

The CPU 22 also has a three-dimensional shape information generating function 22e that generates three-dimensional shape information by using luminance information of a two-dimensional endoscopic image as shape information with which to estimate the shape thereof in a case where the CPU 22 detects a region with an elevation change using the region with elevation change detection function 22a.

Next, the operations that are carried out until polyp detection is performed based on an endoscopic image according to the present embodiment are described.

In the present embodiment, the functions shown in FIG. 4 are implemented by software. More specifically, the CPU 22 reads out a processing program that is stored (held) in the processing program storage section 23, and by performing processing according to this processing program the CPU 22 executes image processing for polyp detection shown in FIG. 5.

When the power of the endoscopic observation apparatus 2 and the image processing device 3 shown in FIG. 1 is turned on, the image pickup apparatus 17 of the endoscope 6 picks up an image, and (a video signal of) an endoscopic image that underwent signal processing at the CCU 8 is displayed on the monitor 9 and is also inputted to the image processing device 3 via the image input section 21.

When a physician operates an image processing start key or the like of an unshown keyboard or the like, that instruction signal is sent to the CPU 22. Thereupon, the CPU 22 starts image processing to perform the polyp detection illustrated in FIG. 5.

First, at step S1, the CPU 22 sets a parameter "i" that indicates the number of an endoscopic image I to the initial value i=1. Next, at step S2, the CPU 22, for example, loads an endoscopic image Ii comprising an $i^{th}$ RGB signal that is sequentially stored in the hard disk 27 or the image storage section 24 shown in FIG. 1.

The series of processes according to the present embodiment are applied to an endoscopic image Ii of respective frames that are inputted consecutively as a moving image. However, the present invention is not limited thereto, and for example, a configuration may be employed in which the image processing shown in FIG. 5 is performed on, for example, endoscopic images at intervals of every several frames. Further, a configuration may also be employed in which the image processing shown in FIG. 5 is performed on endoscopic images that are filed in the hard disk 27 or the like.

After step S2, at step S3 the CPU 22 extracts an R-signal component (abbreviated as "R image") Ri in the endoscopic image Ii. Next, at step S4, the CPU 22 calculates (generates) three-dimensional shape information of the R image Ri based on a change in contrast (change in luminance information). Although according to the present embodiment the CPU 22 calculates the three-dimensional shape information using the R image Ri, additionally, a configuration may be adopted in which the CPU 22 calculates the three-dimensional shape information by using, for example, an image of a luminance signal component.

A processing method that calculates three-dimensional shape information based on the two-dimensional R image Ri is illustrated in FIG. 6.

To calculate three-dimensional shape information on the basis of a two-dimensional image, the CPU 22 estimates (generates) a three-dimensional shape as shown at step S21 in FIG. 6.

As a method of generating the three-dimensional shape, for example, Shape from Shading is available. A method of generating a three-dimensional shape using Shape from Shading is one that utilizes the fact that the intensity of reflected light of a target region that is illuminated by an illumination light from an illumination light source is changed by the state of a gradient of the surface thereof, and reflected light that accompanies that change is reflected in the endoscopic image that is picked up. For example, this method is described in "Reconstructing Shape from Shading with a Point Light Source at the Projection Center-Shape Reconstruction from an Endoscopic Image-", Okatani and Deguchi, Computer vision, pp. 19-26, 1996. Another method that calculates (generates) an estimated three-dimensional shape from a two-dimensional endoscopic image may also be utilized.

Next, at step S22, the CPU 22 calculates a shape index SI and a curvedness CV as feature quantities that represent a curved shape at each curved face of the calculated three-dimensional shape. The shape index SI and curvedness CV are calculated as described below.

With respect to a calculated three-dimensional shape, the CPU 22 calculates first order partial differential coefficients fx, fy, and fz and second order partial differential coefficients fxx, fyy, fzz, fxy, fyz, and fxz for an R pixel value f in a local region (curved face) including the three-dimensional position (x, y, z) of interest.

Using these coefficients, the CPU 22 calculates a Gauss curvature K and a mean curvature H in the manner described in "A study on automated detection of colonic polyps from 3D abdominal CT images based on shape", Kimura, Hayashi, Kitasaka, Mori and Suenaga, Technical Report of IEICE (MI2003-102), pp. 29-34, 2004.

The principal curvatures k1 and k2 (k1≧k2) of the curved face are expressed using the Gauss curvature K and mean curvature H as $$k1 = H + (H^2 - K)^{1/2} k2 = H - (H^2 - K)^{1/2} \quad (1)$$

Further, the shape index SI and curvedness CV as a feature value that represents a curved shape in this case are, respectively, $$SI = \frac{1}{2} - (1/\pi)\arctan[(k1+k2)/(k1-k2)] \quad (2)$$

$$CV = ((k1^2 + k2^2)/2)^{1/2} \quad (3)$$

Thus, the CPU 22 calculates the shape index SI and the curvedness CV for each three-dimensional curved face as three-dimensional shape information.

The shape index SI is expressed by an index having values from 0 to 1 for curved shapes as shown in FIG. 7. In this case, when the shape index SI is 0, the curved shape is concave, and when the shape index SI is 1 the curved shape is convex. That is, the closer the value of the shape index SI is to 1, the more features of a convex elevated shape the region in question has.

Accordingly, by setting a detection standard as a threshold value having the shape index SI value is close to 1, and detecting a region having a shape index SI value larger than this threshold value, it is possible to objectively detect a polyp as an elevated lesion in image processing. In this connection, according to detection standard 1 used at step S10 of FIG. 5 that is described later, (SI=) 0.9 is set as the shape index SI threshold value, and according to detection standard 2 used at step S11, (SI=) 0.8 is set as the shape index SI threshold value.

The curvedness CV represents the inverse number of the curvature radius, and is utilized when limiting the size of a convex shaped region of the target curved face. The processing at step S4 in FIG. 5 is performed in this manner.

According to the present embodiment, when performing image processing for detecting a polyp as an elevated lesion as described below, the CPU 22 uses detection standard 1 and detection standard 2.

At step S5 in FIG. 5, the CPU 22 extracts an R image Ri in the endoscopic image Ii and a G-signal component (abbreviated as G image Gi) in the endoscopic image Ii. Next, at step S6, the CPU 22 performs detection of a color tone change region to detect a region showing a color tone change involving reddening or discoloration.

The processing to detect a region having a color tone change at step S6 is, for example, performed as illustrated in FIG. 8. At the initial step S31, the CPU 22 performs processing to exclude unsuitable pixels such as dark portions, halation or residue from the R image Ri and the G image Gi. To exclude dark portions and halation, exclusion can be simply performed using a threshold value that is set in correspondence to the dark portion and halation. For the residue, it is possible to remove the residue by combining residual color tones with a shape judgment for that portion.

Next, at step S32, the CPU 22 performs processing to divide the region in question into, for example, 8×8 sub-regions.

At step S33, the CPU 22 sets a parameter m that represents the number of a sub-region and a parameter j that represents the number of a pixel inside the sub-region to an initial value 1. In this connection, when numbering the sub-regions, when the proportion of pixels that are excluded by the processing of step S31 that are inside the sub-region exceeds, for example, 50%, that sub-region is excluded from the processing objects (an m number is not allocated thereto). More specifically, unsuitable sub-regions are also excluded from the processing objects.

At step S34, the CPU 22 calculates the chromaticity gj/rj of the $j^{th}$ pixel. In this case, gj represents the luminance level of the $j^{th}$ pixel inside a ($m^{th}$) sub-region of the G image Gi, and rj represents the luminance level of the $j^{th}$ pixel inside a ($m^{th}$) sub-region of the R image Ri. Next, at step S35, the CPU 22 determines whether or not j is the final pixel number jend inside the sub-region. When j does not correspond to jend, at step S36 the CPU 22 increments j by 1 and returns to step S34 to repeat the same processing.

After calculating the chromaticity gj/rj as far as the final pixel number jend in the $m^{th}$ sub-region in this manner, the CPU 22 advances to step S37.

At step S37, the CPU 22 calculates a chromaticity mean value μgrm of the $m^{th}$ sub-region. Next, at step S38, the CPU 22 determines whether or not the number $m^{th}$ of the sub-region is the final number mend. When the number m does not correspond to the final number mend, at step S39 the CPU 22 increments m by 1 and returns to step S34 to repeat the processing of step S34 to S39.

When m matches the final number mend, the CPU 22 proceeds to step S40. At step S40, the CPU 22 calculates the chromaticity mean value μgr for all the sub-regions and the standard deviation σgr.

Next, at step S41, the CPU 22 uses the chromaticity mean value μgr in the case of all sub-regions and the standard deviation σgr to determine whether or not the chromaticity mean value μgrm of the $m^{th}$ sub-region calculated at step S37 indicates that the $m^{th}$ sub-region is a sub-region showing a color tone change involving reddening and discoloration.

More specifically, as shown at step S41, the CPU 22 considers that the chromaticity mean value μgrm of the sub-region is normally distributed, and determines whether or not that chromaticity mean value μgrm is within a range of ±(1.5× σgr) from the distribution position of the chromaticity mean value μgr for all the sub-regions.

When the sub-region in question satisfies the determining condition at step S41, as shown at step S42, the CPU 22 detects (judges) that the sub-region is not a sub-region that shows a color tone change involving reddening and discoloration.

In contrast, when the sub-region does not satisfy the condition at step S41, as shown at step S43, the CPU 22 detects the sub-region as a sub-region showing a color tone change of reddening or discoloration.

More specifically, when the chromaticity mean value μgrm deviates to outside by −1.5×σgr from the distribution position of the chromaticity mean value µgr, the CPU 22 detects (judges) the sub-region as a sub-region showing a color tone change of reddening, and when the chromaticity mean value µgrm deviates to outside by +1.5×σgr from the distribution position of the chromaticity mean value µgr, the CPU 22 detects (judges) the sub-region as a sub-region showing a color tone change of discoloration.

The detection (judgment) result is stored in the information storage section 25 (see FIG. 1) or the like together with the sub-region number m or two-dimensional positional information of the sub-region. That detection result information is utilized for a judgment at step S9 in FIG. 5 that is described below.

In this connection, the processing from steps S41 to S43 in FIG. 8 is performed from 1 to mend by changing the number m of the sub-region. After performing the processing of step S42 or S43 for all sub-regions of the processing object in this manner, the CPU 22 proceeds to the processing of step S7 or step S8 in FIG. 5.

Although an example is described above which uses the chromaticity gj/rj, an arrangement may be used in which bj/gj is added as the chromaticity. In that case, it is possible to support detection of yellow-colored mucous membrane.

Further, in the processing shown in FIG. 8, detection may be performed based on a ratio µrate=µgrm/µgr as the ratio between the chromaticity mean values µgrm and µgr so as, for example, to detect a color tone change as reddening if µrate<0.5 and detect a color tone change as discoloration if µrate>1.5.

Next, at step S7 in FIG. 5, based on three-dimensional shape information calculated at step S4, the CPU 22 performs processing to detect a region with an elevation change. For example, the CPU 22 detects a sub-region section having the aforementioned shape index SI value is 0.8 or more.

Further, at step S8, by associating the three-dimensional shape information obtained at step S4 with information regarding detection of a region with a color tone change that is obtained at step S6, the CPU 22 identifies each pixel or that sub-region included in the region with a color tone change that is detected at step S6, which position corresponds to the position on the three-dimensional shape.

At step S9, the CPU 22 performs judgment processing based on the results obtained at steps S7 and S8. More specifically, the CPU 22 judges whether or not the region with an elevation change on the three-dimensional shape that is detected at step S7 corresponds with the region with a color tone change that is identified at step S8.

If the judgment result at step S9 is No, i.e. if the elevation change is not accompanied by a color tone change, at step S10 the CPU 22 applies polyp detection processing according to detection standard 1.

In contrast, if the judgment result at step S9 is Yes, i.e. if the elevation change is accompanied by a color tone change, at step S11 the CPU 22 applies polyp detection processing according to detection standard 2.

According to the present embodiment, as illustrated in steps S10 and S11, the assessment standard or detection standard for performing polyp detection is changed according to the judgment result at step S9. In this case, since there is a high possibility that the region in question and the periphery thereof is a polyp when a color tone change is detected, by detecting a section having an elevation change feature using detection conditions that are more relaxed than in a case in which a color tone change is not detected, a polyp or a polyp candidate is accurately detected.

Further, although various standards can be applied for polyp detection processing, according to the present embodiment a detection standard according to the aforementioned shape index SI is used.

As the threshold value of the shape index SI for detecting a convex shape (or cup shape) indicating a polyp as an elevated lesion, detection standard 1 is set to (SI=) 0.9 and detection standard 2 is set to (SI=) 0.8 (in this connection, as described above, the nearer the value is to 1, the closer the shape is to a convex shape). At step S10 or S11, the CPU 22 performs a comparison with the 0.9 or 0.8 shape index SI that is the detection standard, and if the value is greater than that value the sub-region is detected (judged) as being a polyp.

In this case, for example, for the curvedness CV, (CV=) 0.2 is taken as the threshold value for both detection standards 1 and 2, and when the value for the relevant sub-region is greater than this value the sub-region is detected (judged) as being a polyp.

Although in the above description the value of the shape index SI as a detection standard changes for a case which is accompanied by a color tone change and a case which is not accompanied by a color tone change, a configuration may also be adopted in which the curvedness CV value is changed to change the detection standard as described below.

More specifically, a configuration may be adopted in which the shape index SI threshold value is set to 0.9 and the curvedness CV threshold value is set to 0.20 as detection standard 1, and the shape index SI threshold value is set to 0.9 and the curvedness CV threshold value is set to 0.15 as detection standard 2.

Further, a change may also be made to lower the shape index SI threshold value and the curvedness CV threshold value of detection standard 2 with respect to detection standard 1.

For example, a configuration may be adopted in which the shape index SI threshold value is set to 0.9 and the curvedness CV threshold value is set to 0.20 as detection standard 1, and the shape index SI threshold value is set to 0.85 and the curvedness CV threshold value is set to 0.15 as detection standard 2.

Thus, at step S10 or step S11 the CPU 22 sets detection standard 1 or 2 as a threshold value and performs polyp detection processing according to the shape index SI value for the region with an elevation change.

The CPU 22 then stores the detection result in association with the endoscopic image Ii of the detection object in, for example, the hard disk 27 shown in FIG. 1, and, for example, displays the detection result side by side with the endoscopic image Ii of the detection object on the display monitor 4 via the display processing section 28.

Subsequently, at step S12 in FIG. 5, the CPU 22 increments i by 1 and performs the same processing for the next endoscopic image Ii.

According to the present embodiment that performs image processing in this manner, it is possible to change (control) a detection standard value or a condition value by referring to color tone change information corresponding to the feature value of a color tone change that occurs incidentally in the case of a polyp, and thereby improve the accuracy (or reliability) of a detection with respect to whether or not a detection object is a polyp. That is, in comparison to the case of image processing that performs polyp detection using only one type of detection, polyp detection can be performed with greater accuracy by combining both kinds of detection.

Although a case is described above in which polyp detection processing is performed at step S10 or step S11 using the threshold value of a shape index SI and a curvedness CV as feature quantities that represent a curved shape, an arrangement may also be adopted in which detection is performed based on information regarding a height from a reference surface in the region with an elevation change.

In this case, when the threshold value for a height in the case of detection standard 1 is taken as H1, it is sufficient to change the detection standard to a threshold value H2 that is less than H1. Thus, when accompanied by a color tone change, highly accurate polyp detection can be performed by changing (controlling) the detection standard so as to relax the detection conditions for the polyp detection.

Although according to the present embodiment a case is described of detecting a polyp as an elevated lesion as a method or means of lesion detection, the present embodiment is not limited thereto, and naturally the present embodiment can also be applied to a depressed lesion.

In this case, for example, in FIG. 5, it is sufficient to change the processing so that at step S7, instead of detecting a region with an elevation change, a depressed lesion region is detected, and to similarly change the processing at step S9.

Further, the detection standards at step S10 and step S11 are also changed to values that are close to the feature value of a depressed lesion. By adopting such changes, the present embodiment can also be applied to a depressed lesion.

Embodiment 2

Next, Embodiment 2 of the present invention is described referring to FIG. 9 to FIG. 13.

In the present embodiment also, a polyp as an elevated lesion is detected by detecting an elevated change region from three-dimensional information (shape information) that is calculated based on a change in contrast.

Figure 9A:
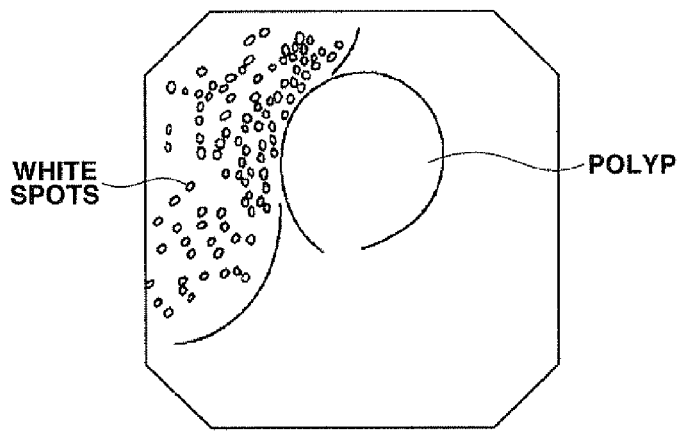
FIG. 9A is a view that illustrates an example of an endoscopic image that is picked up by an image pickup apparatus provided in an endoscope according to Embodiment 2 of the present invention.
Figure 9B:
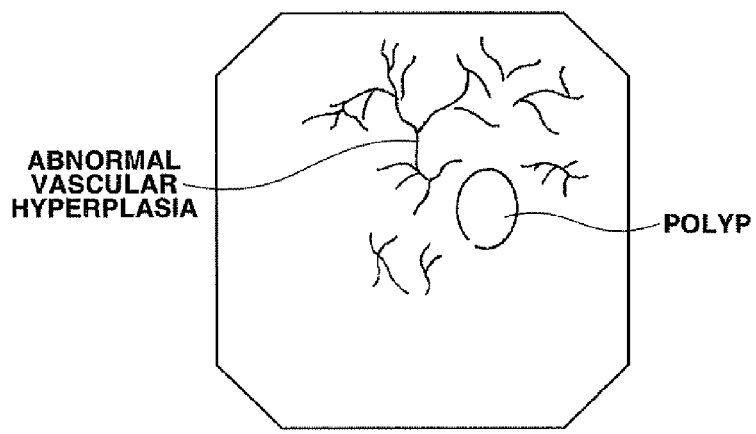
FIG. 9B is a view that illustrates an example of an endoscopic image that is picked up by an image pickup apparatus provided in an endoscope according to Embodiment 2 of the present invention.
Figure 10:
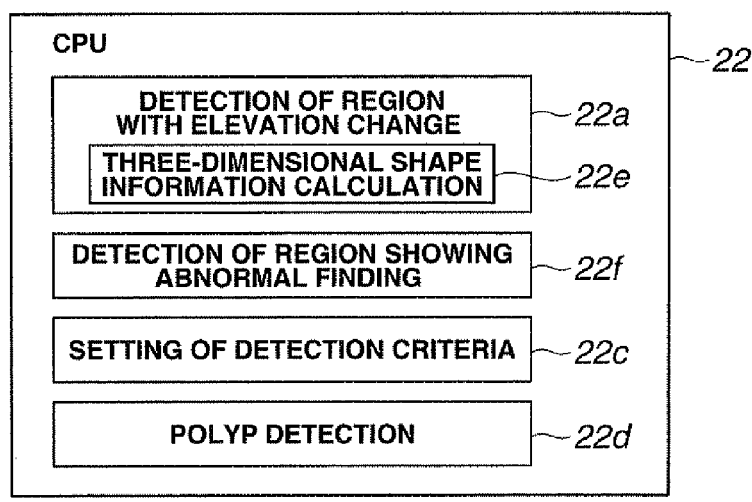
FIG. 10 is a block diagram that illustrates image processing functions performed by a CPU according to Embodiment 2 of the present invention.

There are cases in which a polyp is accompanied by an abnormal finding in peripheral mucous membrane. Conversely, when an abnormal finding is observed in mucous membrane, the possibility that a polyp has developed also increases. Examples of abnormal findings in mucous membrane include white spots as illustrated in FIG. 9A and abnormal vascular hyperplasia as illustrated in FIG. 9B.

According to the present embodiment, attention is focused on such abnormal findings, and when an abnormal finding is present on a mucous membrane surface the accuracy of polyp detection can be improved by changing the detection standard (parameter or threshold value or the like) for polyp detection using shape information.

More specifically, for a region with an elevation change that is accompanied by an abnormal finding in peripheral mucous membrane, detection standards are used in which the detection conditions are more relaxed than in a case in which a region with an elevation change is not accompanied by an abnormal finding.

The configuration of the image processing device 3 according to the present embodiment is the same as in FIG. 1, although the processing contents are different. The CPU 22 in the image processing device 3 according to the present embodiment has the processing functions shown in FIG. 10. More specifically, the CPU 22 according to the present embodiment has a region with abnormal finding detection function 22f instead of the region with color tone change detection function 22b shown in FIG. 4 according to Embodiment 1. In this connection, the abnormal finding region is detected (judged) by processing for a mucosal attribute finding judgment.

Figure 11:
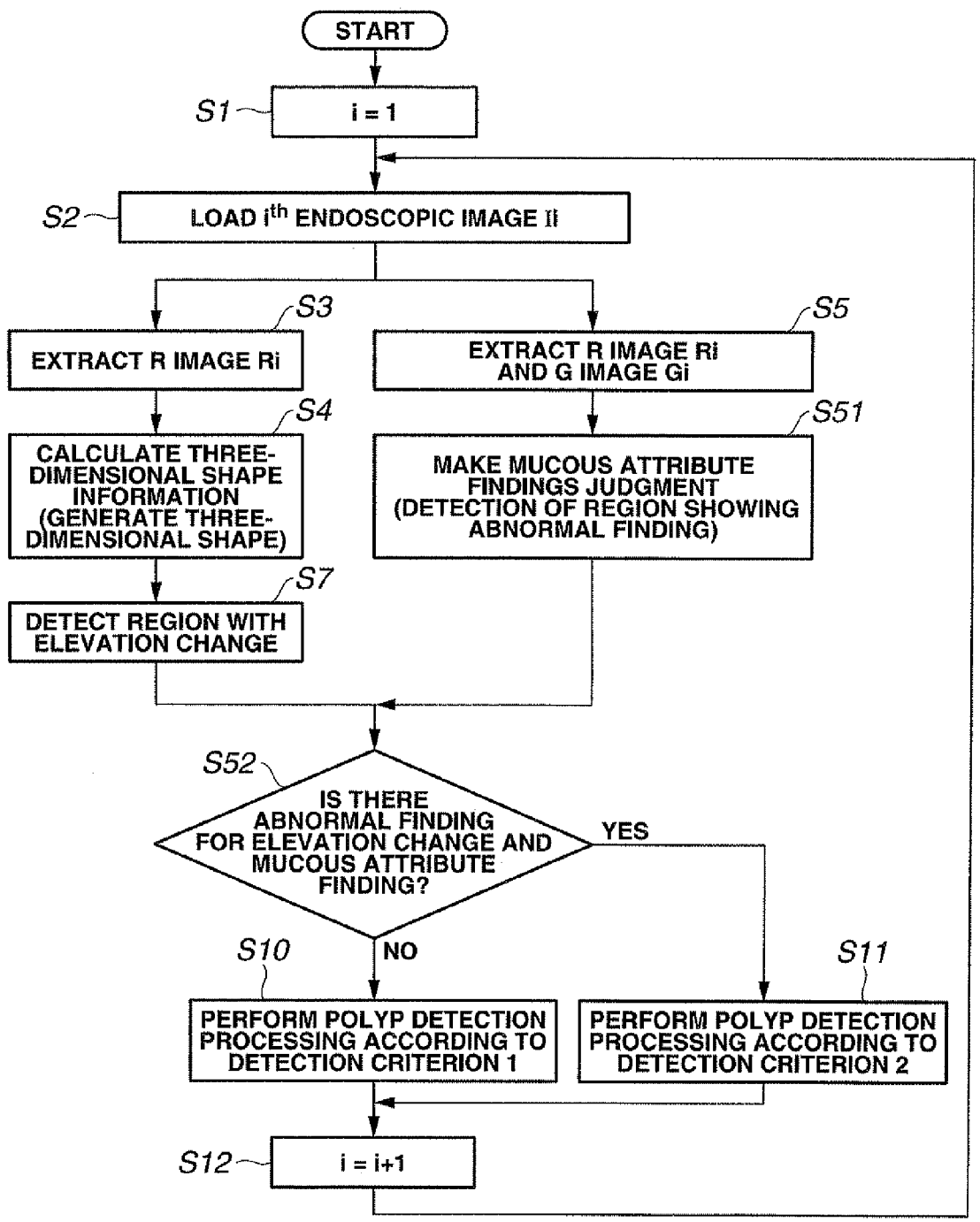
FIG. 11 is a flowchart that illustrates a process that detects a polyp as an elevated lesion by image processing according to Embodiment 2 of the present invention.

Next, referring to FIG. 11, polyp detection operations according to the image processing of the present embodiment are described. Since step S1 to step S5 in the processing of the flowchart shown in FIG. 11 are the same as step S1 to step S5 in the processing of the flowchart shown in FIG. 5, a description thereof is omitted here.

At step S5, the CPU 22 extracts an R image Ri in the endoscopic image Ii and a G image Gi in the endoscopic image Ii. Next, at step S51, the CPU 22 executes processing for a mucosal attribute finding judgment (to detect a region with an abnormal finding).

In the processing for a mucosal attribute finding judgment, the CPU 22 determines whether or not a region presenting a characteristic mucosal attribute finding in the endoscopic image Ii is a region presenting an abnormal finding. According to the present embodiment, by using the R image Ri and G image Gi and applying a series of processes that are described later in step S51 as described above, detection of a region with an abnormal finding such as white spots or abnormal vascular hyperplasia is performed.

Subsequently, similarly to step S7 in FIG. 5, detection of a region with an elevation change is performed based on three-dimensional shape information that is calculated at step S4.

Next, at step S52, the CPU 22 executes judgment processing based on the detection results obtained at steps S51 and S7. If the result of the judgment processing at step S52 indicates no abnormal finding, the CPU 22 advances to step S10. If there is an abnormal finding, the CPU 22 advances to step S11.

Similarly to Embodiment 1, at step S10 the CPU 22 applies polyp detection processing according to detection standard 1. At step S11, the CPU 22 applies polyp detection processing according to detection standard 2. After the processing at steps S10 and S11, the CPU 22 returns to step S2 via step S12.

Various standards can be applied for polyp detection processing. For example, similarly to Embodiment 1, detection may be performed according to the shape index SI or using a curvedness CV threshold value.

The processing for a mucosal attribute finding judgment at step S51 in FIG. 11 according to the present embodiment will now be described referring to the flowcharts shown in FIG. 12 and FIG. 13.

Figure 12:
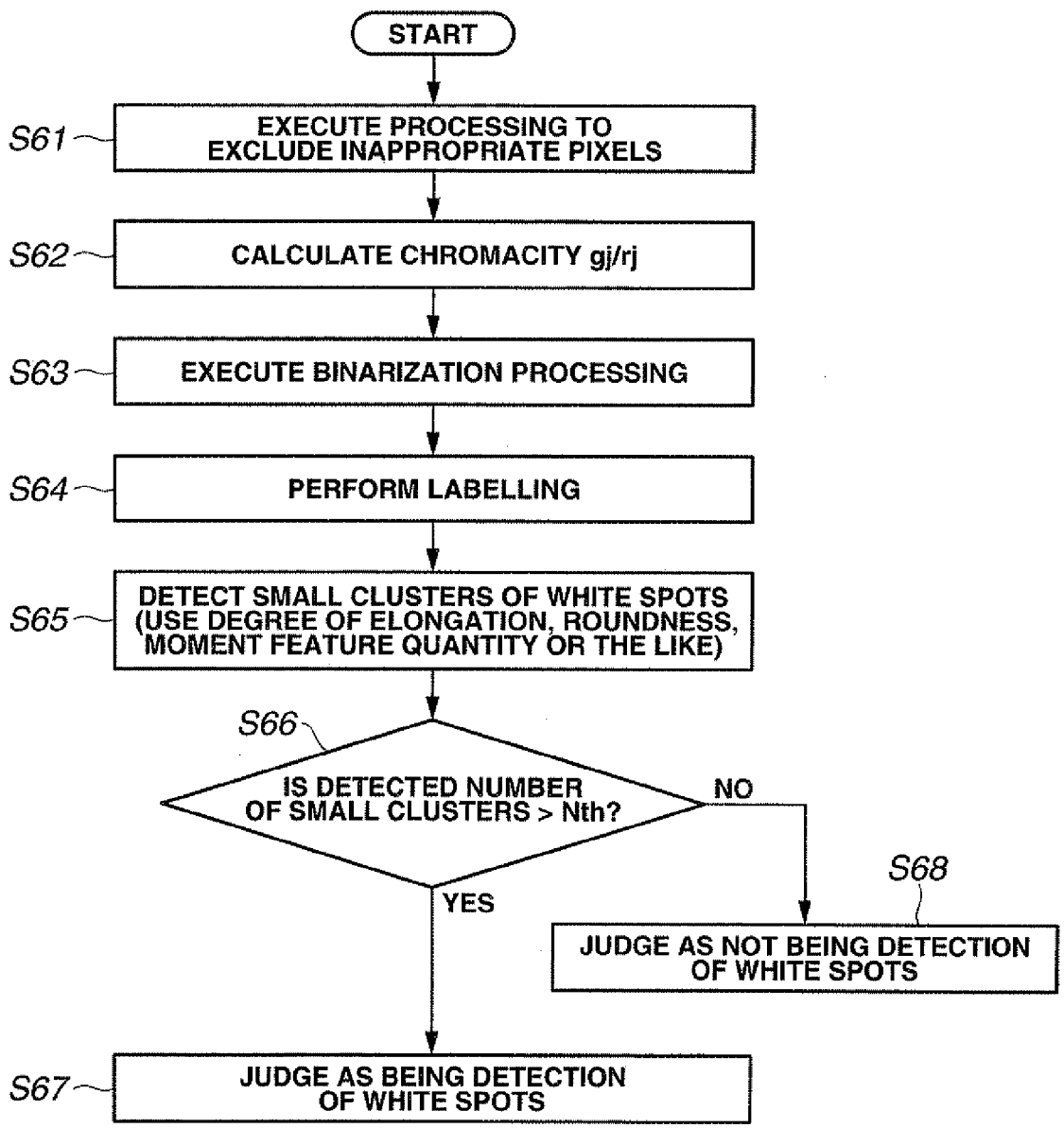
FIG. 12 is a flowchart that illustrates the processing contents of a mucosal attribute information judgment at S51 in FIG. 11.
Figure 13:
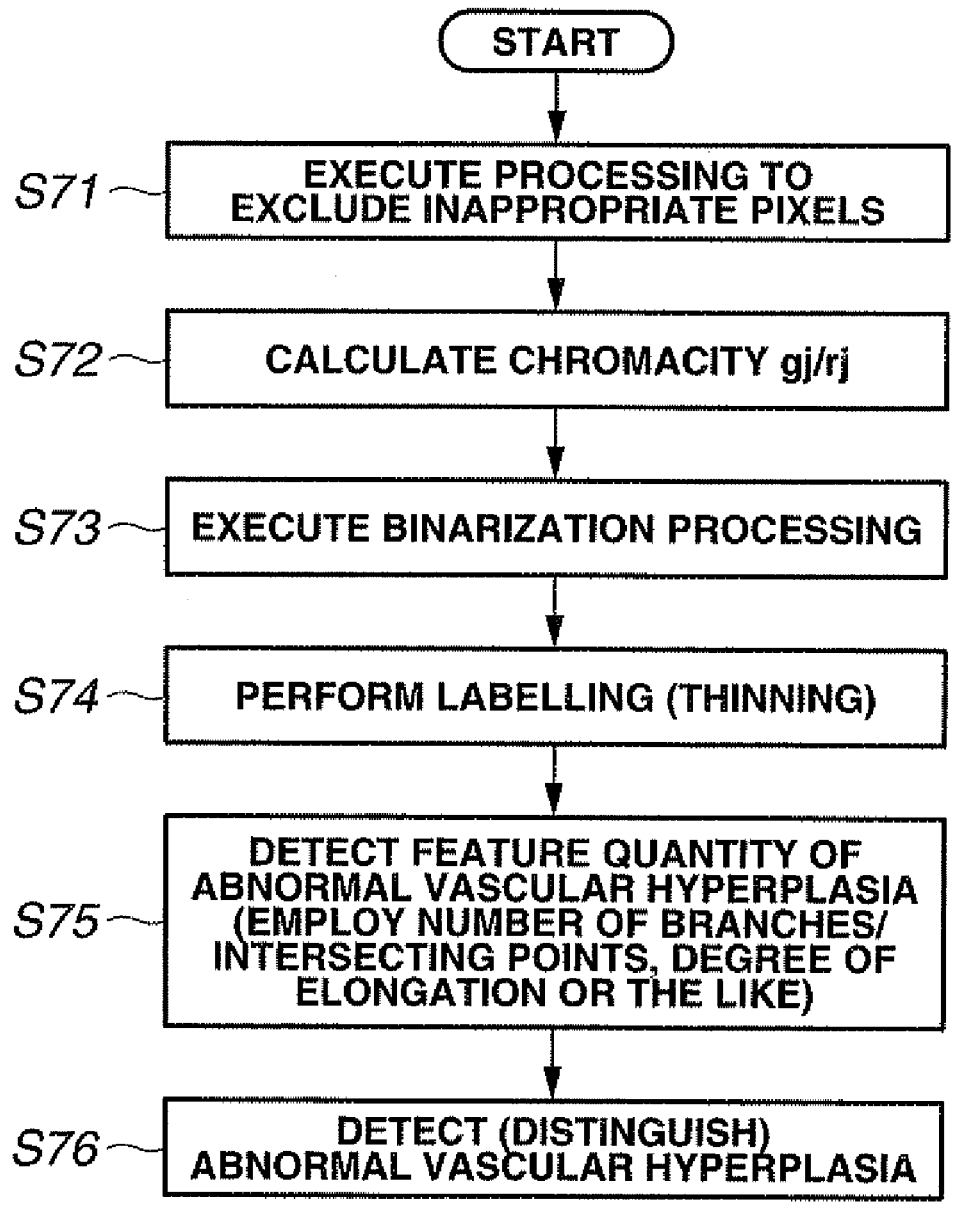
FIG. 13 is a flowchart that illustrates the processing contents of an abnormal vascular hyperplasia judgment at step S51 in FIG. 11.

As mucosal attribute finding judgment processing, according to the present embodiment, processing to detect an abnormal finding of white spots that is illustrated in FIG. 12 and processing to detect an abnormal finding of abnormal vascular hyperplasia that is illustrated in FIG. 13 are executed. First, the processing to detect an abnormal finding of white spots illustrated in FIG. 12 is described.

Initially, at step S61, the CPU 22 performs processing to exclude unsuitable pixels such as dark portions, halation, and residue. Next, at step S62, the CPU 22 calculates the chromaticity gj/rj of each pixel. Here, the suffix "j" represents the pixel number.

At step S63, the CPU 22 executes binarization processing using threshold value processing. In this case, for example, a (chromaticity) threshold value Vth is set to 0.8 to perform binarization using this threshold value Vth. In the binarization, 1 is set if $gj/rj > 0.8$, and 0 is set if otherwise, i.e. if $gj/rj \leq 0.8$. In this manner, a binarization image is generated.

Subsequently, at step S64, the CPU 22 performs labeling processing that tracks pixels for which a binarization value is 1 in the binarization image to label the region and generate a labeling image from the binarization image.

Next, at step S65, the CPU 22 performs processing to detect small clusters of white spots with respect to the labeling image that is generated by the labeling processing. That is, the CPU 22 performs detection of small clusters of white spots to detect whether or not clusters corresponding to small clusters caused by white spots occur in the labeling image.

When performing the detection of small clusters of white spots, for example, the CPU 22 uses the degree of elongation (=area/thinning length). The CPU 22 then detects a degree of elongation value E for the labeling image and performs a comparison to determine whether or not the value E is less than the (judgment standard) threshold value Vth (for example, Vth=10). The CPU 22 then calculates a number of small clusters N such that E<Vth (=10).

In this connection, a configuration may be adopted in which the CPU 22 calculates the number of small clusters N using the roundness or moment feature quantity or the like as a detection standard instead of the degree of elongation.

Next, at step S66, the CPU 22 judges whether or not the number of small clusters N detected at step S65 is larger than a threshold value Nth (for example, Hth=20) of the detection standard for white spot detection. When the condition N>Nth is fulfilled, as shown at step S67, the CPU 22 judges that white spots are detected in the labeling image (G image Gi and R image Ri). Conversely, when the condition N>Nth is not fulfilled, at step S68 the CPU 22 judges that white spots are not detected.

The detection result at step S67 and step S68 is utilized for the judgment at step S52. That is, the detection result is utilized to indicate the existence or non-existence of an abnormal finding according to the existence or non-existence of a white spot detection.

Further, as the mucosal attribute finding judgment processing at step S51, processing to detect an abnormal finding due to abnormal vascular hyperplasia as illustrated in FIG. 13 that is described next is performed. In order to detect abnormal vascular hyperplasia, processing is performed that detects localized thick blood vessels and minute complex branching from the endoscopic image Ii.

From the initial step S71 to step S74, the CPU 22 performs processing that is substantially the same as that shown in FIG. 12. More specifically, at step S71, the CPU 22 performs processing to exclude unsuitable pixels such as dark portions, halation, and residue, at step S72 the CPU 22 calculates the chromaticity gj/rj of each pixel, and at step S73 the CPU 22 performs binarization processing according to threshold value processing. In this case, the CPU 22 performs binarization using a threshold value Vth that is different from the case illustrated in FIG. 12.

For example, the CPU 22 sets the threshold value Vth to 0.2, and uses this threshold value Vth to perform binarization in which 1 is set if gi/rj<0.2, and 0 is set if otherwise, i.e. if gi/rj≧0.2. In this manner, a binarization image is generated.

The CPU 22 performs labeling processing at the subsequent step S74. In this case, the CPU 22 creates a thin line image as a labeling image.

Next, at step S75, the CPU 22 performs processing to detect a feature value corresponding to abnormal vascular hyperplasia. For the feature value detection processing, the CPU 22 detects the number of branches/intersecting points with respect to the thin line image. Next, at step S76, the CPU 22 determines the existence or non-existence of an abnormal vascular hyperplasia detection by using a threshold value for the number of branches/intersecting points or a discriminant function.

In this connection, as the feature value detection processing, instead of performing the processing using the number of branches/intersecting points, a configuration may be adopted in which, by using the degree of elongation or the like, the CPU 22 detects the number of times the degree of elongation exceeds the threshold value and performs detection (judgment) of abnormal vascular hyperplasia according to whether or not that number exceeds a threshold value for abnormal vascular hyperplasia detection.

The detection result obtained by the processing shown in FIG. 13 is utilized for the judgment at step S52. At step S52, the CPU 22 judges whether or not a region with an elevation change that is detected at step S7 is one accompanied by, as a mucosal attribute finding thereof, the detection of white spots according to the processing shown in FIG. 12 or accompanied by the detection of abnormal vascular hyperplasia according to the processing shown in FIG. 13.

The processing performed by the CPU 22 after the result of judgment processing obtained at step S52 is the same as the processing in the case of Embodiment 1 that is shown in FIG. 5.

More specifically, when the judgment processing at step S52 indicates that the region with an elevation change is not accompanied by an abnormal finding, at step S10 the CPU 22 performs polyp detection by applying detection standard 1. In contrast, when the judgment processing indicates the region with an elevation change is accompanied by an abnormal finding, at step S11 the CPU 22 performs polyp detection by applying detection standard 2. After the processing at step S10 and step S11, the CPU 22 increments the image parameter i by 1, and performs the same processing for the next endoscopic image Ii.

For the detection standard 1 and the detection standard 2, detection is performed using the shape index SI or using a curvedness CV threshold value as described above.

In this connection, for the foregoing description, a configuration may also be adopted in which a detection filter for detecting white spots or abnormal vascular hyperplasia is applied with respect to the G image Gi, to thereby detect white spots or abnormal vascular hyperplasia.

Further, when a region with an abnormal finding such as white spots or abnormal vascular hyperplasia is detected over a plurality of frames, the detection standard can be changed (controlled) so as to perform polyp detection that applies detection standard 2 with respect to the other frames also.

Thus, according to the present embodiment, it is possible to perform highly accurate detection of a polyp by performing polyp detection as elevated lesion detection by changing the detection standard with respect to a region with an elevation change according to a case in which an abnormal finding is detected and a case in which an abnormal finding is not detected by processing that judges a mucosal attribute finding.

The order of the image processing in FIG. 11 may be changed. For example, the processing of step S7 may be performed prior to the processing of step S51. Further, in order to reduce the amount of calculation, a configuration may be adopted in which the processing that judges a mucosal attribute finding at step S51 is performed for a region corresponding to a detection region of a non-elevation change portion that does not show a three-dimensional elevation at step S7. That is, since a region with an abnormal finding in the present embodiment incidentally arises at the periphery of a polyp as an elevated lesion, a configuration may be adopted that detects an abnormal finding for a peripheral mucous membrane or a flat part on the periphery of the region with an elevated lesion change.

The detection standards 1 and 2 are not limited to a case applying detection according to the shape index SI or a curvedness CV threshold value as described above, and as described in Embodiment 1, a configuration may be adopted that detects an elevated lesion based on the value of a height from a reference surface or the like. In this case also, when a polyp is accompanied by white spots or abnormal vascular hyperplasia on a mucous membrane surface, control is performed so as to increase the sensitivity for polyp detection, thereby enabling highly accurate polyp detection.

The lesion detecting means and lesion detection method according to the present embodiment are not limited to the case of an elevated lesion, and can be similarly applied to a depressed lesion as described in Embodiment 1.

In the above described Embodiment 1 and Embodiment 2, a case is described in which, when detecting a lesion by image processing, the detection standard when detecting a lesion candidate such as an elevated lesion region based on luminance information is changed in accordance with the detection result when a region (i.e. an incidental region) with a color tone change or an abnormal finding is detected. However, a configuration may also be adopted so as to detect lesions in a comprehensive manner based on the two detection results.

Further, as another detection method or detection means for these embodiments, a configuration may be adopted so as to detect whether or not a lesion candidate is a lesion in accordance with whether or not a region exists in which there is a correlation between the two detection results. For example, to respond to demands to detect only regions for which it is considered there is a sufficiently high possibility that a candidate is a lesion, the accuracy of lesion section detection can be increased by detecting a region as a lesion candidate in a case where a correlation exists between the two results that detect the region in question as a lesion candidate.

Although according to Embodiment 1 and Embodiment 2 a technique that is based on estimating a three-dimensional shape is described as a lesion detecting technique, the present invention is not limited thereto. For example, an arrangement can also be considered that applies a technique that, after extracting an edge by band pass filtering with respect to a two-dimensional R image, performs binarization using threshold value processing, and then detects an edge that shows a circular arc shape presenting a polyp-like lesion by known Hough transformation.

In this case also, it is possible to change the detection standard based on an abnormal finding at the periphery or the lesion by employing the length, area or curvature of an arc or the like of the edge that is detected as a lesion candidate as a detection standard.

Although a technique that is based on threshold value processing with respect to the curvedness CV and the shape index SI is described in the aforementioned embodiments as a lesion detection technique, the present invention is not limited thereto. For example, without performing threshold value processing, it is possible to prepare image groups having findings of respective shapes such as a convex shape or a cup shape as training data, and utilize these for a detection technique employing a discrimination circuit that uses each feature value that is calculated. For example, in a case where an abnormal finding is present when using a discriminator that uses a known linear discriminant function, control that facilitates detection of a convex shape or the like can be performed by controlling the weighting for values obtained by application of a linear discriminant function for each shape.

It is to be understood that a modified example of the above described embodiments in which the embodiments are partially combined or in which the image processing order is changed is also included in the scope of the present invention.

According to the present invention as described above, a candidate region of a lesion such as a polyp is detected based on luminance information in a medical image having color information such as an endoscopic image, and an incidental region that is accompanied by a color tone change such as reddening or a discoloration portion that arises because of incidental attributes that accompany a lesion is also detected. Thus, highly accurate lesion detection can be performed by changing the detection standard for detecting a lesion from the lesion candidate region according to the detection result for the incidental region.

What is claimed is:

1. A medical image processing device, comprising:
a three-dimensional surface shape generation section that generates a three-dimensional surface shape reflecting a surface shape of an observation target in a medical image based on a two-dimensional image obtained from at least one color signal in the medical image including a plurality of color signals;
a lesion candidate region detecting section that detects a lesion candidate region which comprises a region with an elevation change or a region with a depression change, utilizing information of the three-dimensional surface shape that is generated by the three-dimensional surface shape generation section;
an incidental region detecting section that detects an incidental region that arises because of incidental attributes accompanying a lesion from the medical image; and
a detection standard changing section that changes a detection standard when detecting a lesion from the lesion candidate region in accordance with a detection result of the incidental region;
wherein the detection standard changing section uses, as the detection standard, a first detection standard when the incidental region is not detected, and a second detection standard which is more relaxed than the first detection standard when the incidental region is detected.

2. The medical image processing device according to claim 1, wherein the incidental region detecting section detects a region with a color tone change that presents attributes of a color tone change such as reddening or discoloration as the incidental region.

3. The medical image processing device according to claim 1, wherein the incidental region detecting section detects a region with an abnormal finding that presents attributes of an abnormal finding of white spots or abnormal blood vessels as the incidental region.

4. The medical image processing device according to claim 2, wherein the detection standard changing section changes, as the detection standard, a threshold value of at least one of a shape index and a curvedness of a feature value that represents a curved shape in the information of the three-dimensional surface shape that is generated.

5. The medical image processing device according to claim 1, wherein the detection standard changing section changes, as the detection standard, a threshold value of a height from a reference surface or at least one of a shape index and a curvedness of a feature value that represents a curved shape in the information of the three-dimensional surface shape that is generated.

6. The medical image processing device according to claim 1, wherein in a case where the three-dimensional surface shape of the lesion candidate region detected by the lesion candidate region detecting section is a convex or concave shape, when the incidental region is detected by the incidental region detecting section, the detection standard changing section uses the second detection standard with a degree of the convex or concave shape more relaxed than that in the first detection standard which is used when the incidental region is not detected.

7. A medical image processing device, comprising:
a three-dimensional surface shape generation section that generates a three-dimensional surface shape reflecting a surface shape of an observation target in a medical image based on a two-dimensional image obtained from at least one color signal in the medical image including a plurality of color signals;
a lesion candidate region detecting section that detects a lesion candidate region which comprises a region with an elevation change or a region with a depression change, utilizing information of the three-dimensional surface shape that is generated by the three-dimensional surface shape generation section;
an incidental region detecting section that detects an incidental region that arises because of incidental attributes accompanying a lesion from the medical image; and
a lesion detecting section that performs lesion detection based on existence or non-existence of a region in which a lesion candidate region that is detected by the lesion candidate region detecting section and an incidental region that is detected by the incidental region detecting section correlate.

8. A medical image processing method, comprising:
a three-dimensional surface shape generation step that generates a three-dimensional surface shape reflecting a surface shape of an observation target in a medical image based on a two-dimensional image obtained from at least one color signal in the medical image including a plurality of color signals;
a lesion candidate region detection step that detects a lesion candidate region which comprises a region with an elevation change or a region with a depression change, utilizing information of the three-dimensional surface shape that is generated by the three-dimensional surface shape generation step;
an incidental region detection step that detects existence or non-existence of an incidental region that arises because of incidental attributes accompanying a lesion from the medical image; and
a detection standard changing step that changes a detection standard when detecting a lesion from the lesion candidate region according to a detection result regarding existence or non-existence of the incidental region;
wherein the detection standard changing step uses, as the detection standard, a first detection standard when the incidental region is not detected, and a second detection standard which is more relaxed than the first detection standard when the incidental region is detected.

9. The medical image processing method according to claim 8, wherein the incidental region detection step detects a region with a color tone change that presents attributes of a color tone change of reddening or discoloration as the incidental region.

10. The medical image processing method according to claim 8, wherein the incidental region detection step detects a region with an abnormal finding that presents attributes of white spots or abnormal blood vessels as the incidental region.

11. The medical image processing method according to claim 8, wherein the detection standard changing step changes, as the detection standard, a threshold value of at least one of a shape index and a curvedness of a feature value that represents a curved shape in the information of the three-dimensional surface shape that is generated.

12. The medical image processing method according to claim 8, wherein in a case where the three-dimensional surface shape of the lesion candidate region detected in the lesion candidate region detecting step is a convex or concave shape, when the incidental region is detected in the incidental region detecting step, the detection standard changing step uses the second detection standard with a degree of the convex or concave shape more relaxed than that in the first detection standard which is used when the incidental region is not detected.

* * * * *